US00PP18248P2

(12) United States Plant Patent
Olesen

(10) Patent No.: US PP18,248 P2
(45) Date of Patent: Nov. 27, 2007

(54) MINIATURE ROSE PLANT NAMED 'POULPAR045'

(50) Latin Name: ***Rosa* hybrid**
Varietal Denomination: Poulpar045

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 24 days.

(21) Appl. No.: 11/442,558

(22) Filed: May 26, 2006

(51) Int. Cl.
*A01H 5/00* (2006.01)

(52) U.S. Cl. ..... Plt./116

(58) Field of Classification Search ..... Plt./116, Plt./118, 119
See application file for complete search history.

*Primary Examiner*—Kent Bell
*Assistant Examiner*—Annette H Para

(57) ABSTRACT

A new miniature rose plant that has abundant, yellow orange flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar045'.

SUMMARY OF THE INVENTION

The present invention constitutes a new and distinct variety of miniature rose plant which originated from a controlled crossing between the female seed parent, an unnamed seedling, and the male pollen parent, a non-patented variety by the same inventor named 'Poulpal022'.

The two parents were crossed during the summer of 2003 and the resulting seeds were planted in a controlled environment in Fredensborg, Denmark. The new variety, named 'Poulpar045', originated as a single seedling from the stated cross.

The new variety may be distinguished from its female seed parent by the following combination of characteristics:

1. The seed parent has fewer petals than 'Poulpar045'.
2. Flowers of the seed parent have a general tonality of a pure yellow color while flowers of 'Poulpar045' are yellow-orange.

The new variety may be distinguished from its male pollen parent by the following combination of characteristics:

1. The pollen parent is less compact in growth habit than 'Poulpar045'.
2. 'Poulpar022' has orange flowers while 'Poulpar045' has yellow-orange flowers.

The objective of the hybridization of this rose variety for commercial culture was to create a new and distinct variety with unique qualities, such as:

1. Uniform and abundant yellow flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar045' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar045' was selected by the inventor as a single plant from the progeny of the hybridization in 2003

Asexual reproduction of 'Poulpar045' by vegetative cuttings and traditional budding was first done by Mogens N. Olesen in the nursery in Fredensborg, Denmark in June of 2004. This initial and other subsequent propagation cycles conducted in controlled environments have demonstrated that the characteristics of 'Poulpar045' are true to type and are transmitted from one generation to the next.

BRIEF DESCRIPTION OF THE DRAWING

The accompanying color illustration shows as true as is reasonably possible to obtain in color photographs of this type, the typical characteristics of the claimed plant. Specifically illustrated in the drawing are flowers, flower buds, flower parts, leaves, and stems.

DETAILED DESCRIPTION OF THE VARIETY

Figure 1:
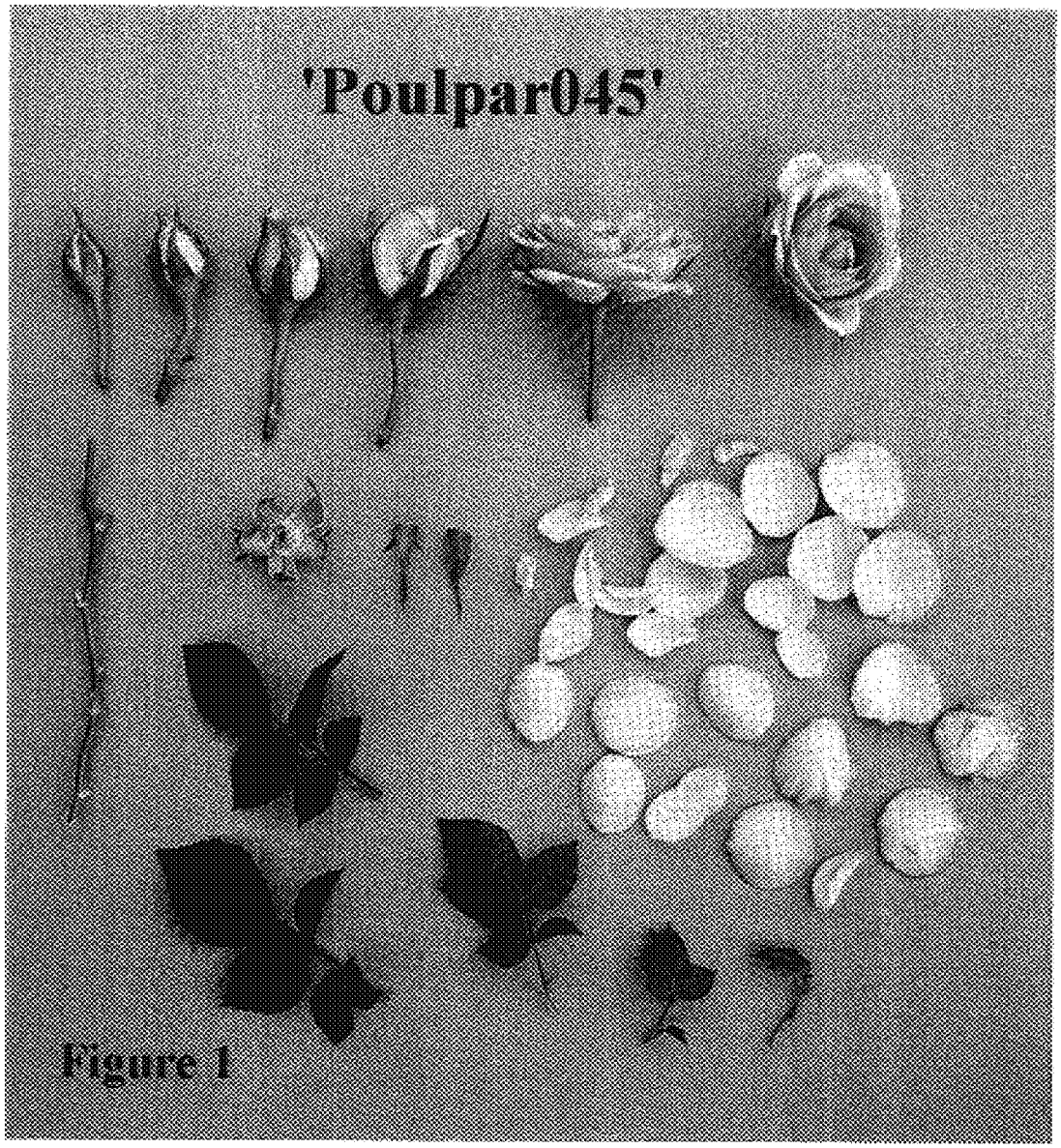

The following is a description of 'Poulpar045', as observed in its growth in a glasshouse in Burlington, Ontario, Canada. Observed plants are 4 months of age and were cultivated in 10.5 cm pots. Color references are made using The Royal Horticultural Society (London, England) Colour Chart, 2001, except where common terms of color are used.

For a comparison, several physical characteristics of the rose variety 'Poulmist', U.S. Plant patent application Ser. No. 10/916,341, now abandoned, are compared to 'Poulpar045' in Chart 1.

CHART 1

| | 'Poulpar045' | 'Poulmist' |
|---|---|---|
| Petal Count: | 50 to 60 total, 20 to 25 of which are petaloids | 35 to 40 petals under normal conditions with 3 to 4 petaloids |
| General Tonality of Flower Color: | Yellow-Orange Group 14C with intonations of Yellow-Orange Group 16A to 21B towards the flower center | Yellow Group 12B |

FLOWER AND FLOWER BUD

Blooming habit: Recurrent.

Flower bud:

*Size.*—Upon opening, 20 to 21 mm in length from base of receptacle to end of bud. Typically 12 mm in diameter.

*Bud form.*—Broadened ovate with a pointed apex.

*Bud color.*—As sepals unfold, petals are Yellow-Orange Group 14C with intonations of Yellow Group 6D and Yellow-Orange Group 16A to 16B. The margins of some petals are Orange-Red Group 35A to Red Group 42B.

*Sepals.*—Upper Surface: Color: Green Group 138A. Texture: Moderately pubescent. Lower Surface: Color: Yellow Green Group 147A to 147B. Texture: Smooth. Shape: Apex: Cirrhose. Base: Flat at union with receptacle. Margins: Margins have strong medium foliaceous appendages on three of the five sepals. Size: Typically 30 mm long by 6 mm wide.

*Receptacle.*—Surface Texture: Smooth. Shape: Urn-shaped. Size: Typically 7 mm in height by 7 mm wide. Color: Yellow Green Group 144A to 144B.

*Pedicel.*—Surface: Smooth. Length: 17 to 20 mm average length. Diameter: 2.5 mm on average. Color: Yellow-Green Group 144B. Strength: Medium strength.

*Borne.*—Normally a single flower per flowering branch.

Flower bloom:

*Fragrance.*—Light floral fragrance.

*Duration.*—As a pot plant, flowers last from 21 to 28 days. Petals fall cleanly away from plant after they have passed maturity.

*Size.*—Flower diameter is 45 to 55 mm when open. Flower depth is typically 25 mm.

*Form.*—Double petaled flower with a high pointed center which remains tightly closed for about half of the duration of flower opening. Shape of flower, side view: Upon opening, the upper portion is flat. The lower portion is a flattened convex. After opening, the upper portion is flattened convex. The lower portion is concave.

*Petalage.*—There are normally 50 to 60 total, 20 to 25 of which are petaloids.

Flower color:

*Upon opening and after opening, petals.*—Outermost and Innermost Petals: Upper Surface: Yellow Group 10A to Yellow Group 12B with intonations of Orange-Red Group 35A observed on some petal margins. Lower Surface: Yellow Group 13B blended with intonations of Yellow Group 7B. Some petal margins are colored Orange-Red Group 35A.

*Basal petal spots.*—No distinctive coloration at petal base observed.

General tonality: On open Yellow-Orange Group 14C with intonations of Yellow-Orange Group 16A to 21B towards the flower center.

Petals:

*Petal reflex.*—Slightly.

*Petal margin.*—Entire. With weak undulations of margin.

*Shape.*—Generally orbicular. Base: Obtuse and acute. Apex: Rounded.

*Size.*—Variable. Outer petals are typically 26 mm long by 29 mm wide. Inner petals are typically 25 mm long by 20 mm wide.

*Thickness.*—Average.

*Texture.*—Smooth.

Petaloids:

*Quantity.*—Normally, there are 20 to 25 in quantity.

*Size.*—Normally 16 mm long; 11 mm wide.

*Shape.*—Irregular with very strong undulations of margin.

*Color.*—Color observations for petaloids are the same as the petals.

Reproductive organs:

*Pollen.*—None observed.

*Anthers.*—Size: 2 mm long. Color: Yellow Group 5C with intonations of Yellow-Orange Group 15B at margins. Quantity: 45 on average.

*Filaments.*—Color: Yellow Group 12A. Length: 3 to 4 mm.

*Pistils.*—Length: 5 mm long. Quantity: Typically 30.

*Stigmas.*—Superior relative to the length of the filaments and the height of the anthers. Color: Yellow Group 6D.

*Styles.*—Color: Yellow Group 11D with intonations of Red Group 41D.

*Seed formation.*—Not observed.

PLANT

Plant growth: Vigorous, very compact, upright and moderately bushy. When grown on its own roots, the average height of the plant itself is 17 to 20 cm and the average width is 10 to 12 cm.

Stems:

*Color.*—Young wood: Yellow-Green Group 144B. Older wood: Yellow-Green Group 144A to 144B.

*Internodal distance.*—21 to 30 mm.

*Length of stems.*—From the base of the stem to the flowering portion, normally 12 to 14 cm.

*Diameter.*—Typically 2 to 3 mm.

*Surface texture.*—Young wood: Smooth. Older wood: Smooth.

Prickles:

*Incidence.*—2 to 4 per 10 cm of stem.

*Size.*—Average length is 3 mm.

*Color.*—Juvenile prickles are Yellow-Green Group 144D. Mature prickles are Greyed-Orange Group 177A.

*Shape.*—Linear.

Plant foliage: Normal number of leaflets on normal leaves in middle of the stem: 5 leaflets.

*Compound leaf size.*—55 to 80 mm (l)×40 to 55 mm (w).

*Quantity.*—5 leaves per 10 cm of stem.

*Color.*—Juvenile foliage: Upper Leaf Surface: Yellow-Green Group 144A to 144B. Lower Leaf Surface: Yellow-Green Group 144B. Anthocyanin: Greyed-Red Group 178A located on the margins of leaflets.

Mature foliage: Upper Leaf Surface: Yellow-Green Group 147A. Lower Leaf Surface: Yellow-Green Group 147B.

Plant leaves and leaflets:

*Stipules.*—Size: 6 to 12 mm in length. Shape: Linear, slightly broad based with outward extending apecies. Margins: Finely serrated with many stipitate glands. Color: Yellow-Green Group 146A to 146B.

*Petiole.*—Length: 17 mm in length by 1 mm in diameter. Color: Upper Surface: Yellow-Green Group 144A with occasional anthocyanic pigments the color of Greyed-Red Group 179A. Lower Surface: Yellow-Green Group 144B.

*Rachis.*—Size: Normally 20 to 25 mm in length. Color: Upper Surface: Yellow-Green Group 144A with occasional anthocyanic pigments the color of Greyed-Red Group 179A. Lower Surface: Yellow-Green Group 144B.

*Leaflet.*—Size: 28 to 36 mm length by 18 to 26 mm wide. Margin: Serrate. General Shape: Elliptical. Apex Shape: Acute. Base Shape: Round. Texture: Smooth. Arrangement: Odd pinnate. Venation: Reticulate. Leaf Gloss: Matte.

Disease resistance: Average resistance to powdery and downy mildew, black spot, and *Botrytis* under normal growing conditions in Burlington, Ontario, Canada.

It is claimed:

1. A new and distinct variety of rose plant of the miniature class named 'Poulpar045', substantially as illustrated and described herein, due to its abundant, yellow orange flowers, vigorous growth, compact habit, suitability for production from softwood cuttings in pots, and durable flowers and foliage that make the variety suitable for distribution in the floral industry.

* * * * *